United States Patent [19]

Summers et al.

[11] Patent Number: 5,695,519
[45] Date of Patent: Dec. 9, 1997

[54] PERCUTANEOUS FILTER FOR CAROTID ANGIOPLASTY

[75] Inventors: David P. Summers, Montgomery; Gary Ball, Spring, both of Tex.

[73] Assignee: American Biomed, Inc., The Woodlands, Tex.

[21] Appl. No.: 565,256

[22] Filed: Nov. 30, 1995

[51] Int. Cl.⁶ .................................................. A61B 17/00
[52] U.S. Cl. .................................................. 606/200
[58] Field of Search ......................... 606/159, 170, 606/171, 180, 200, 1, 108; 604/22; 128/898, 899

[56] References Cited

U.S. PATENT DOCUMENTS 4,790,812 12/1988 Hawkins, Jr. et al. ................. 606/159
4,790,813 12/1988 Kensey ..................................... 606/159
4,842,579 6/1989 Shiber .
4,873,978 10/1989 Ginsburg ................................. 606/200
4,926,858 5/1990 Gifford, III et al. .
4,950,238 8/1990 Sullivan .................................. 606/159
4,979,951 12/1990 Simpsom ................................. 606/159

Primary Examiner—William Lewis
Attorney, Agent, or Firm—Nick A. Nichols, Jr.

[57] ABSTRACT

A distal intravascular filter is disclosed for filtering blood flow therethrough and entrapping and retaining embolic debris. The intravascular filter including a small diameter hollow guide wire or tube capable of percutaneous placement of the distal end thereof beyond a carotid stenosis. The distal portion of the tube includes a filter mounted thereon. The filter is deployable from a tightly closed configuration to an open circumference for blocking the unfiltered flow of blood beyond the carotid stenosis. The filter is deployable between open and closed positions by manipulation of an actuating wire extending from the filter and out the proximal end of the tube.

9 Claims, 2 Drawing Sheets

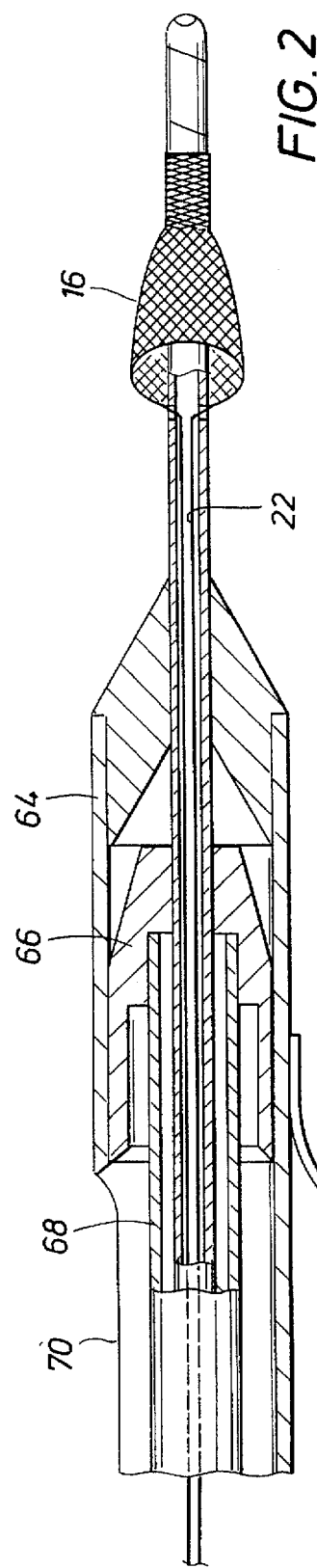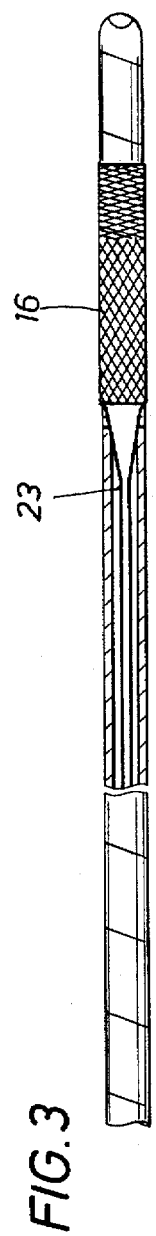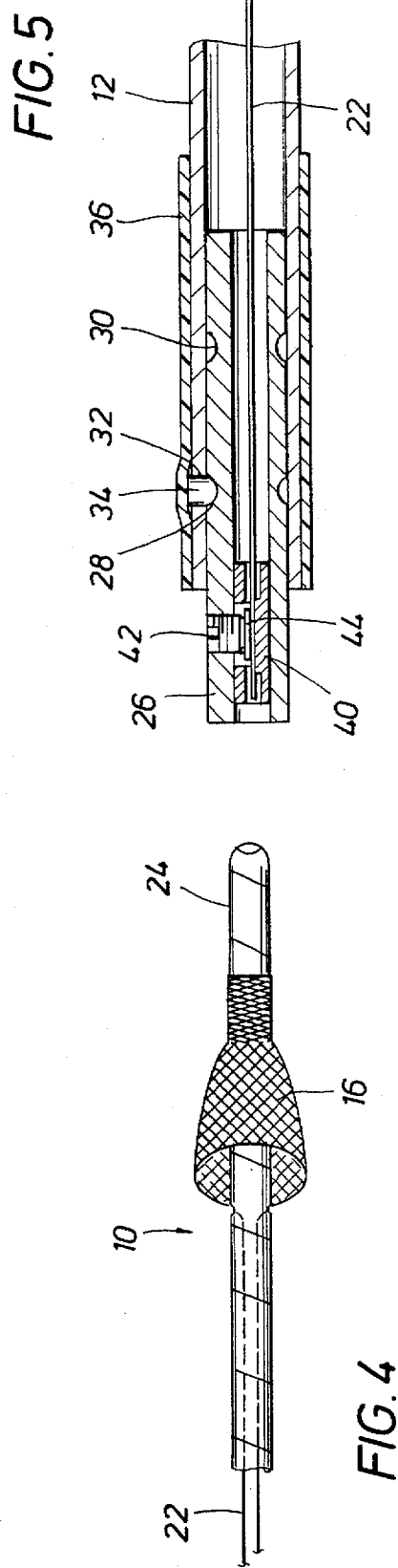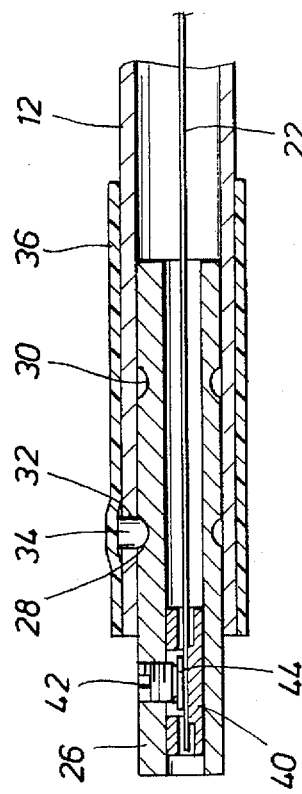

PERCUTANEOUS FILTER FOR CAROTID ANGIOPLASTY

BACKGROUND OF THE DISCLOSURE

The present invention is directed to an apparatus and method for carotid angioplasty, particularly, a deployable filter device for use in percutaneous interventions in the vascular tree of the head and neck.

Many technological advancements have been made in recent years in the treatment of coronary disease. For example, various prior art devices have been developed for removing and/or compressing atherosclerotic plaque, thrombosis, stenosis, occlusions, clots, embolic material, etc. from veins, arteries and the like. Some attempts have been made to control the circulatory loss of emboli. In U.S. Pat. No. 4,842,579, a flexible guidewire insertable into an artery is equipped with a distal barrier to counter distal movement of obstructive material while the cutting blade cuts the obstructive material. In U.S. Pat. No. 4,926,858, an atherectomy catheter includes a distal retention member which forms a cap for the cutter to retain collected atheroma materials. However, while percutaneous interventions are presently much more common in treating coronary disease, little has been done to utilize these technological advancements in the vascular tree of the head and neck.

The medical community has recognized for sometime that a leading source of serious disability among adults is new or recurrent strokes. Ischemic stroke (encompassing thrombotic and embolic episodes) accounts for 80% to 85% of all stroke cases, with the remaining 15% to 20% accounted for by hemorrhagic stroke. In the last few years, awareness in the medical community has dramatically increased that the infusion of a thrombolytic agent within six (6) hours of the onset of ischemic stroke can significantly improve a patient's short and long term prognosis. Yet, until recently, little was done prophylactically to palliate the condition which contributes most stroke, the stenotic carotic artery.

Recent studies indicate that percutaneous interventions are being performed in the vascular tree of the head and neck. Such studies indicate that surgical intervention of the symptomatic carotid stenosis provides significant protection against stroke in patients with high grade stenosis. Carotid endarterectomy for asyemptomatic patients with 60% stenosis but in surgically good health has been recommended. Carotid angioplasty, however, is significantly less expensive than carotic endarterectomy, but to date only a few studies relating to carotid angioplasty have been done and those patients were mainly refractory to other therapies. Although angioplasty for carotid stenosis is appealing particularly in the cost containment in managed care environment, it is unlikely that it will become a mainstream procedure until sufficient clinical results are demonstrated. One reason for lack of strong sponsorship for angioplasty has been the rather high rate of morbidity, mainly transient ischemic attacks, resulting from the dislodgment of the intra-arterial emboli during the procedure. Thus, carotid endarterectomy, because of outstanding clinical results, continues to be the procedure of choice for symptomatic carotid atherosclerosis.

It is therefore one object of the present invention to provide a solution to the problem of distal embolism in angioplasty. The present invention prevents the circulatory loss of emboli by entrapping particles which have been dislodged either by thrombolysis, surgery or angioplasty.

It is a further object of the invention to trap fragments of plaque or other embolic material broken off or lost by angioplasty, atherectomy, stenting or surgery, in a filter which collapses in a manner to entrap and retain the fragments while the filter is removed from the body.

It is yet another object of the invention to provide an intravascular temporary filter deployable from a small diameter guidewire or catheter capable of remotely opening within an artery, thereby preventing the migration of stroke causing blood clots to various organs of the human body. The filter is remotely actuated to a closed position for retaining the entrapped material and removal from the artery without spillage.

SUMMARY OF THE INVENTION

A distal intravascular filter is disclosed for filtering blood flow therethrough and entrapping and retaining embolic debris. The intravascular filter comprises a small diameter hollow guide wire or tube capable of percutaneous placement of the distal end thereof beyond a carotid stenosis. The distal portion of the tube includes a filter mounted thereon. The filter is deployable from a tightly closed configuration to an open circumference for blocking the unfiltered flow of blood beyond the carotid stenosis. The filter is deployable between open and closed positions by manipulation of an actuating wire extending from the filter and out the proximal end of the tube.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 2 is a partial side view of the filter of the invention deployed to an open position;

FIG. 3 is a partial side, cross-sectional view depicting the filter of the invention in a closed position;

FIG. 4 is a partial side view of the filter of the invention deployed in an open configuration; and FIG. 5 is a partial sectional view of the actuating mechanism of the invention.

DETAILED DESCRIPTION OF THE PREFERRED EMBODIMENT

Figure 1:
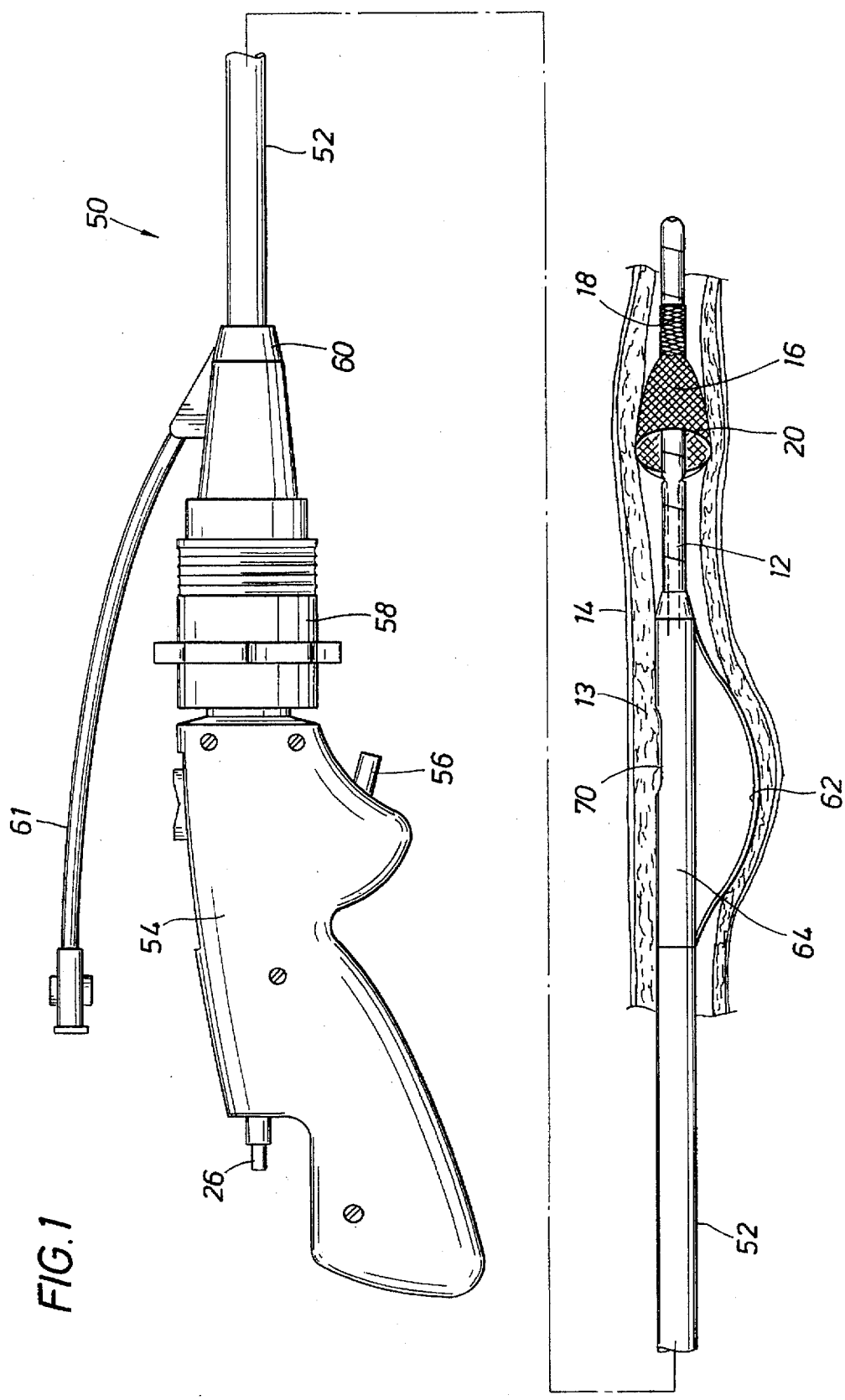
FIG. 1 is an environmental, partial sectional view depicting the intravascular filter of the invention located within the carotid artery.

Referring first to FIG. 1, the percutaneous temporary filter of the invention is shown, for illustrative purposes, used in an atherectomy procedure. It is understood however that the percutaneous temporary filter of the invention is suitable for use for trapping fragments of plaque or other embolic material broken off or lost by angioplasty, atherectomy, stenting or surgery.

The percutaneous filter apparatus of the invention, generally identified by the reference number 10, comprises a small diameter hollow cored wire or tube 12 capable of percutaneous placement of the distal end of the tube 12 beyond the carotid stenosis 13 in the carotid artery 14. A deployable filter 16 is mounted to the distal end of the tube 12. The filter 16 at its forward most end is tied and bonded to the tube 12 at 18. The tube 12 extends through the filter 16. The proximal end of the filter 16 is open and defined by a rim 20 formed about a deployment wire 22. The rim 20 is formed by overlapping the proximal edge of the filter 16 about the wire 22 and forming an enclosure or hem by sewing the overlapped portion of the filter onto itself.

The wire 22 comprises an elastic memory wire extending from the filter 16 through the tube 12 and exiting the proximal end thereof. The memory wire 22 includes a portion which is slightly crimped or bent at 23 so that upon advancement of the wire 22 into the tube 12, the wire 22 forms the expandable rim 20 which engages the inner wall of the artery 14. The tube 12 may be several feet in length. The distal end 24 of the tube 12 is flexible thereby aiding the tube 12 to navigate through the artery 14. The proximal end of the tube 12 is closed by a detent sleeve 26 as best shown in FIG. 5. The detent sleeve 26 is slidably received within the proximal end of the tube 12. The detent sleeve 26 includes a pair of recesses 28 and 30 formed on the exterior surface of the detent sleeve 26. The proximal end of the tube 12 is provided with an opening 32 supporting a detent button 34 therein. The proximal end of the tube 12 is encased within a silastic sleeve 36 which provides a non-slip gripping area and resiliency for the detent button 34.

The wire 22 extends through the tube 12 and terminates at the detent sleeve 26 and is anchored therein. The wiring anchoring assembly comprises an anvil 40 which is hollow so that the wire 22 extend through the anvil 40. A set screw 42 extending through the wall of the detent sleeve 26 anchors the wire 22 to the anvil 40. A compression disk 44 is interposed between the set screw 42 and the wire 22 for firmly securing the wire 22 between the set screw 42 and the anvil 40.

The wire 22 is forwardly advanced to deploy the filter 16 by gripping the silastic sleeve 36 and pushing the sleeve 26 forward into the tube 12. The silastic sleeve 36 provides resiliency permitting the detent button 34 to move radially out of the detent 30 as the sleeve 26 is advanced forwardly. Upon alignment with the detent 28, the detent button 34 is received therein and thereby indicating that the filter 16 is fully deployed.

Referring now to FIGS. 1 and 2, the percutaneous filter apparatus 10 of the invention is shown used in conjunction with an atherectomy catheter generally identified by the reference numeral 50. The catheter 50 comprises a flexible catheter tube 52 which may be several feet in length. The proximal end of the catheter tube 52 is connected to a handle 54. The handle 54 houses a motor and battery assembly. An on/off switch is provided for activating the motor to operate the catheter 50.

The catheter 50 includes a wire actuation ring 58 and a seal housing 60. The wiring actuation ring 58 is slideably mounted about the seal housing 60. The wire actuation ring 58 is connected to the distal end of a pair of wires 62 which extend through the catheter tube 52. The wires 62 are connected to the forward tip of the cutter housing 64 forming the distal end of the catheter tube 52. The wires 62 extend exterior of the cutter housing 64 and upon actuation of the ring 58 bow outwardly, as shown in FIG. 1, for moving the cutter housing 64 laterally against the interior arterial wall of the artery 14. Housed within the cutter housing 64 is a cutting element 66 which is mounted to the distal end of a drive shaft 68 operatively connected to the drive motor assembly housed within the handle 54. The cutter housing 64 is provided within an elongate cutting window or port 70.

A cannula 61 is connected to the seal housing 60. The cannula 61 defines a passageway in fluid communication with the catheter tube 52. Once the cutter housing 64 is properly positioned in the region of the carotid stenosis 13, aspirator means, such as a vacuum pump, is connected to the cannula 61 for aspirating severed or excised plaque or the like as it is severed from the wall of the artery 14. A collection vessel is connected to the cannula 61 for receipt of the aspirated cuttings.

Referring again to FIG. 1, the use and operation of the percutaneous filter apparatus 10 in conjunction with the atherectomy catheter 50 will be described. Typically, the catheter 50 is inserted through the femoral artery of the patient and is directed by the physician to the site of the obstruction. As shown in FIG. 1, the tube 12 is inserted through the hollow drive shaft 68 of the catheter 50 so that the distal end of the tube 12 extends out of the end of the cutter housing 64. Alternatively, the tube 12 may be initially inserted into the artery and directed to the site of the obstruction and placed so that the filter 16 is positioned beyond the site of the obstruction. The catheter 50 may thereafter be inserted in the artery of the patient over the tube 12. Once the cutting head 64 is properly positioned, the filter 16 is deployed radially outwardly by pushing the sleeve 26 inwardly to advance the wires 22, thereby deploying the rim 20 radially outwardly into contact with the inner surface of the artery 14.

The deployed filter 16 blocks the unfiltered flow of blood beyond the obstruction in the carotid artery. The size of the filter media of the filter 16 is such that blood flow is not significantly reduced through straining but embolic debris that may be released by the cutting action of the cutter 66 is trapped and retained by the filter 16. Once the procedure is complete and the obstruction is removed, the sleeve 26 is retracted thereby pulling the wire 22 to collapse the filter 16 so that it is tautly closed about the tube 12. Any embolic debris is thereby trapped within the filter 16 as the tube 12 is removed from the artery 14. Thus, angioplasty, atherectomy, stenting or thrombolysis may be safely carried out in the carotid artery without fear of accidental dislodgment of stroke causing clots. It is understood that the percutaneous filter apparatus 10 is not limited to use in conjunction with a catheter. For example, the percutaneous filter apparatus 10 may be used during open surgery by placing the filter 16 beyond the surgical shout and only withdrawing the filter 16 after the surgery has been completed and the surgeon feels comfortable that reprofusion has stabilized.

While the foregoing is directed to the preferred embodiment of the present invention, other and further embodiments of the invention may be devised without departing from the basic scope thereof, and the scope thereof is determined by the claims which follow.

What is claimed is:

1. A percutaneous filter, comprising:
   a) a hollow tube;
   b) a deployable filter mounted about the distal end of said hollow tube, wherein said filter includes an expandable rim at the proximal end thereof and is bonded to said hollow tube at the distal end of said filter; and
   c) actuating means for deploying the filter from a collapsed position to an open position.

2. The apparatus of claim 1 wherein said actuating means comprises an elastic memory wire extending through said hollow tube and forming said expandable rim of said filter.

3. The apparatus of claim 1 wherein said memory wire expands radially outwardly through an opening in said hollow tube to form said expandable rim of said filter.

4. An atherectomy catheter for removal of occlusive material in a blood vessel, tract, or cavity comprising:

(a) a catheter tube;
(b) a cutter head assembly attached to the distal end of said catheter tube;
(c) drive means extending through said catheter tube;
(d) cutter means mounted within said cutter head assembly and connected to said drive means;
(e) power means operatively connected to said cutter means;
connected to said catheter tube for evacuating excised occlusive material from the vessel;
(g) a hollow guide wire extending through said catheter and exiting the distal end thereof;
(h) a deployable filter mounted about the distal end of said hollow guide wire; and
(i) actuating means mounted at the proximal end of said hollow guide wire for deploying said filter from a collapsed position to an open position.

5. The apparatus of claim 4 wherein said filter is bonded to said hollow tube at the distal end thereof and includes an expandable rim at the proximal end of said filter.

6. The apparatus of claim 5 wherein said actuating means comprises an elastic memory wire extending through said hollow tube and forming said expandable rim of said filter.

7. The apparatus of claim 6 wherein said memory wire expands radially outwardly through an opening in said hollow tube to form said expandable rim of said filter.

8. A percutaneous filter, comprising:

a) a hollow tube;
b) a deployable filter mounted about the distal end of said hollow tube, wherein said filter includes an expandable rim at the proximal end thereof and is bonded to said hollow tube at the distal end of said filter; and
c) actuating means for deploying the filter from a collapsed position to an open position, wherein said actuating means comprises an elastic memory wire extending through said hollow tube and forming said expandable rim of said filter.

9. A method for removing occlusive material in a blood vessel, tract or cavity, comprising the steps of:

a) advancing a hollow guide wire having deployable filter means mounted on the distal end thereof into the blood vessel to a position beyond the occlusion;
b) advancing cutter means over the guide wire into the blood vessel to a position for removing the occlusion, said cutter means including means for removing severed occlusive material from the site of the occlusion;
c) deploying said filter means radially outwardly into contact with the blood vessel wall;
d) rotating said cutter means and thereby severing the occlusive material and removing severed material from the site of the occlusion;
e) trapping severed material released into the blood flow by the cutting action of said cutter means, said released severed material trapped and retained by said filter means;
f) collapsing said filter means about said hollow guide wire; and
g) withdrawing said cutter means and said filter means with the trapped severed material from the blood vessel.

* * * * *